United States Patent [19]
Rochette et al.

[11] Patent Number: 5,749,385
[45] Date of Patent: May 12, 1998

[54] METHOD AND APPARATUS FOR LOOSELY RETAINING INSTRUMENTS IN A WASHING SYSTEM RACK ASSEMBLY

[75] Inventors: Daniel Rochette; John Wood, both of Charlesbourg; Christian Angers, Ancienne-Lorette, all of Canada

[73] Assignee: Steris Corporation, Mentor, Ohio

[21] Appl. No.: 756,438

[22] Filed: Nov. 26, 1996

[51] Int. Cl.$^6$ ............................... B08B 3/02; B08B 9/02
[52] U.S. Cl. ........................ 134/199; 134/170; 134/171
[58] Field of Search .................................. 134/199, 170, 134/171, 169 R, 54, 166 C; 422/63, 292, 300, 104, 28; 220/DIG. 19, DIG. 6

[56] References Cited

U.S. PATENT DOCUMENTS

| Re. 16,839 | 12/1927 | Bork | 134/171 |
|---|---|---|---|
| 457,603 | 8/1891 | Fox | 134/54 |
| 4,064,886 | 12/1977 | Heckele | 134/171 |
| 4,417,596 | 11/1983 | Pahlen | 134/199 |
| 4,730,631 | 3/1988 | Schwartz | 134/170 |
| 4,748,007 | 5/1988 | Gaudion et al. | 134/170 |
| 5,279,317 | 1/1994 | Bowman et al. | 134/170 |
| 5,288,467 | 2/1994 | Biermaier | 134/170 |
| 5,310,524 | 5/1994 | Campbell et al. | 134/170 |
| 5,603,342 | 2/1997 | Shambaugh | 134/170 |

OTHER PUBLICATIONS

*3M Cannulated Instrument cleaning system*, 3M Health Care ©3M 1995.
*The Endo–Clean™ System*, Snowden–Pencer USA ©1993.
*Desinfizieren und Reinigen von MIC–und Micro–Instrumentarium*, Miele Professional.
*Spexialkorb zur Aufbereitung van starren Endoskopen*, BHT Hygiene Technik GMBH.
*RIWO–GRIP–Basket 38 050.001*, Wolf.

*Primary Examiner*—Amy B. Vanatta
*Attorney, Agent, or Firm*—Fay, Sharpe, Beall, Fagan, Minnich & McKee

[57] ABSTRACT

A plurality of spray arms (26, 28) are rotatably supported in a washing chamber (14) for spraying a washing and rinsing fluid. An instrument basket (32) is positioned within the washing chamber for retaining instruments or equipment (44) to be washed. An instrument holder (38) associated with the instrument basket loosely holds an instrument (44). The instrument holder includes a tube body (74) having a cavity (80) for receiving an end portion of the instrument (44) and a flange (86) positioned on an external surface of the tube body (74). A retainer cap (76) has an outer wall (116) biased resiliently outwardly over the flange (86) and resilient end wall (118) covering an open end portion of the cavity (80). The end wall has a central aperture (120) which resiliently yields to the end portion of the instrument (44) when inserted in the cavity (80) and which loosely retains the end portion of the instrument in the cavity (80) during a washing and rinsing operation. The end wall (118) also includes at least one slit (122) which defines a number of flap portions (124) which resiliently yield to the instrument when inserted in the cavity (80) and which loosely retain the end portion in the cavity during a washing and rinsing operation. The washer (10) also includes a second instrument basket (42) removably positioned within the instrument basket (32). The second instrument basket (42) includes a second instrument holder (40) similar to the first instrument holder (38).

21 Claims, 8 Drawing Sheets

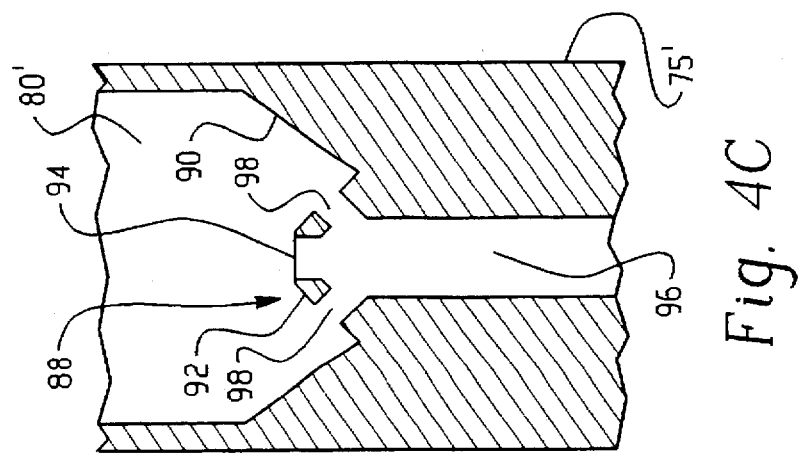
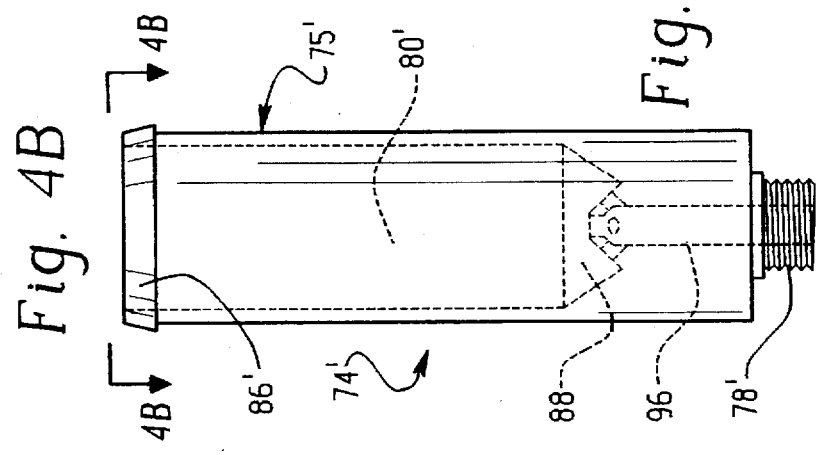
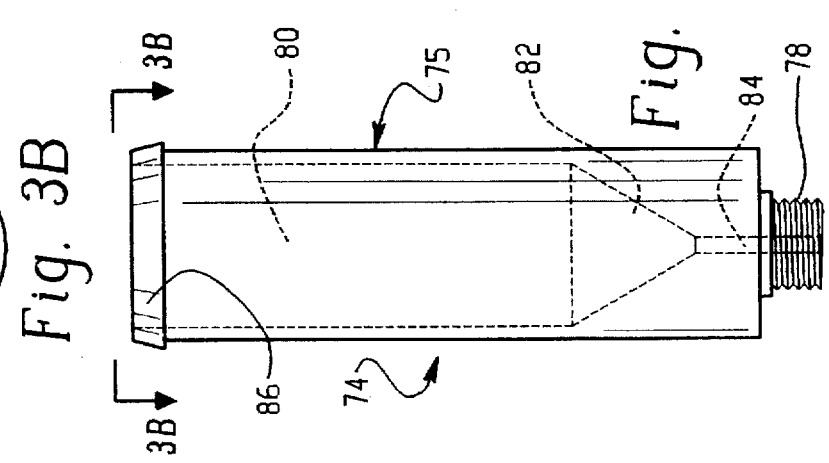

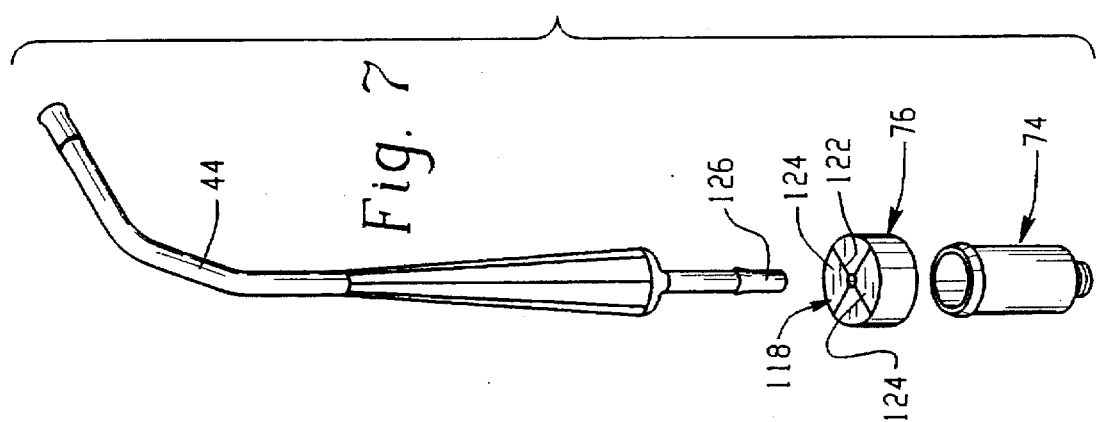
Fig. 7
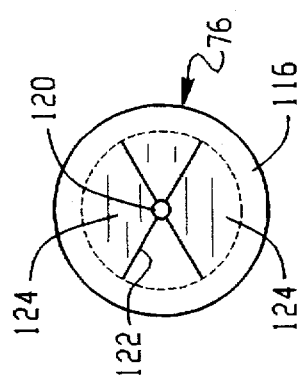
Fig. 6B
Fig. 6A
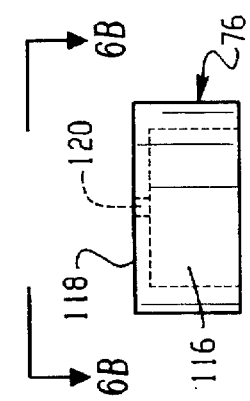
Fig. 5C
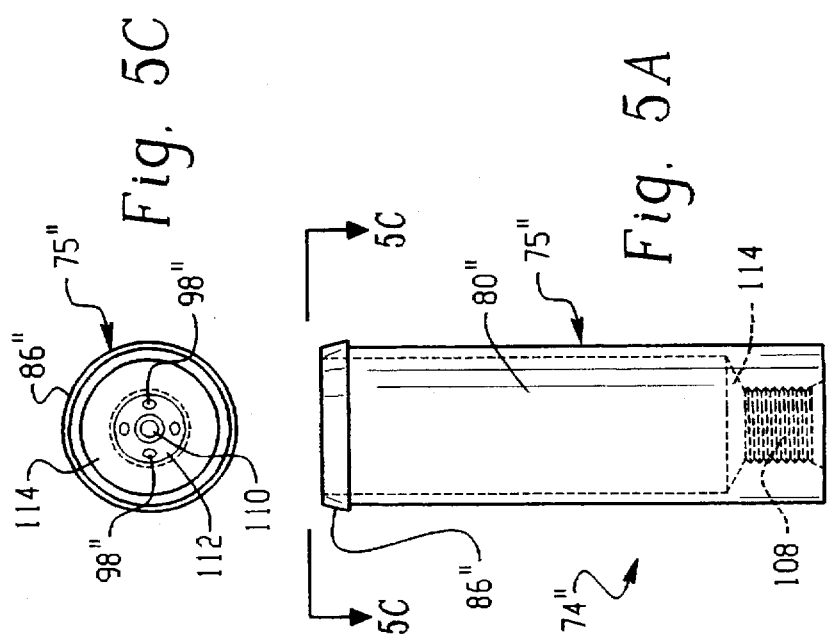
Fig. 5A
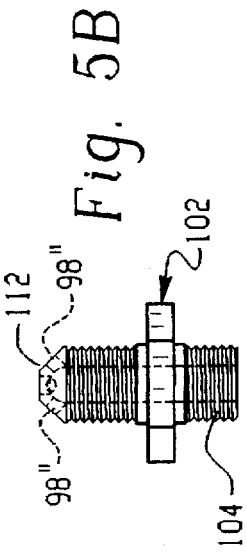
Fig. 5B

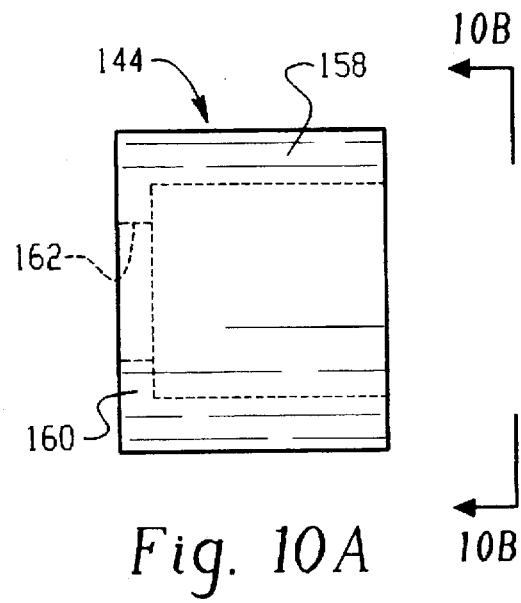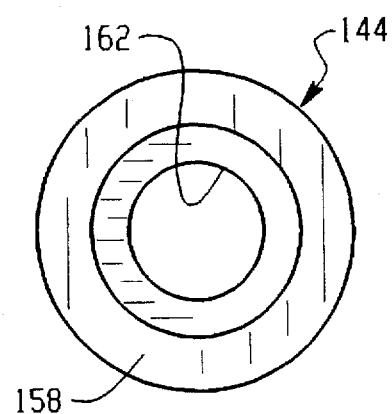
Fig. 10A    Fig. 10B
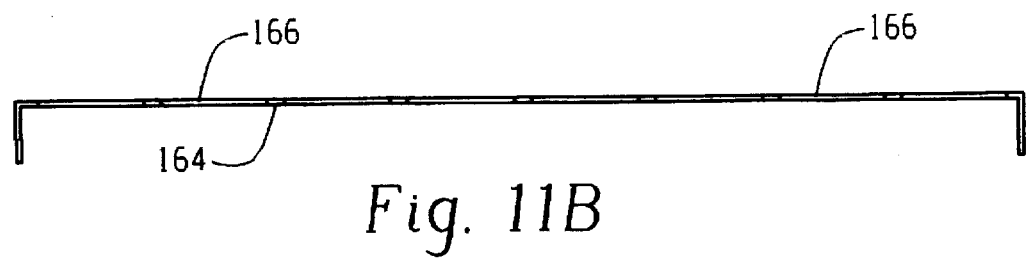
Fig. 11B
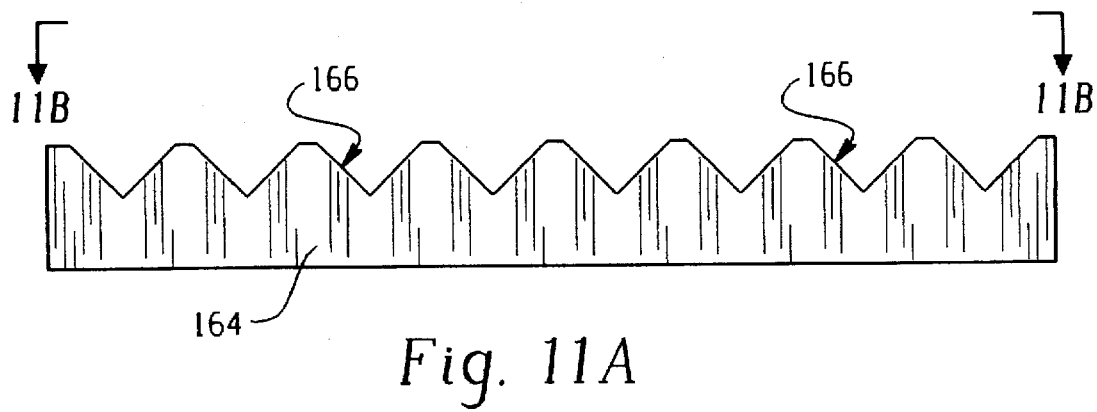
Fig. 11A 5,749,385

METHOD AND APPARATUS FOR LOOSELY RETAINING INSTRUMENTS IN A WASHING SYSTEM RACK ASSEMBLY

BACKGROUND OF THE INVENTION

The present invention relates to the cleaning and decontaminating art. It finds particular application in conjunction with washers for washing instruments and equipment such as surgical, medical, dental, veterinary, and mortuary instruments and equipment which contain, or potentially contain, biological contaminants and will be described with reference thereto. It is to appreciated that the invention will also find application in conjunction with washing, sanitizing, and disinfecting equipment of various types.

In order to wash instruments and equipment exposed to biological contaminants completely, each surface of the instruments and equipment must be thoroughly exposed to a cleaning solution. In particular, when hollow tubular instruments or equipment such as suction tips or cannulas are to be washed, it is important that the inner walls defining a longitudinal bore therethrough as well as the walls defining an outer surface are contacted with washing and rinsing fluid.

Known washing systems typically include baskets or racks which retain the various instruments and equipment to be washed. However, when tubular equipment is placed in a basket, there is no assurance that enough washing liquid will flow through the bore to clean it, particularly for long thin bores. Other racks include a vertical tube which loosely positions a hollow instrument in a position such that the bore of the instrument is proximate a nozzle through which washing and rinsing fluid is forcibly discharged. Thus, washing and rinsing fluid discharged from the nozzle at least in part is directed through the bore of the hollow instrument thereby contacting the inner walls defining the bore. In addition, a portion of the washing and rinsing fluid discharged from the nozzle is directed around and along the outer surface of the instrument thereby contacting the exterior surfaces of the instrument. However, loosely positioned instruments are sometimes thrown out of the vertical tube by the force of the nozzle. This not only terminates the flow of liquid through the base, but may damage the instrument.

To prevent the instruments from being thrown around by the force of the wash water nozzles, the prior art retainer mechanisms typically clamp at least a portion of the instrument or equipment. While the clamp holds the instrument in place, it also prevents the washing and rinsing fluid from reaching the portion of the instrument under the clamp. As another example, one end of the instrument can be received in a friction or threaded fitting around the nozzle. The fitting abuttingly contacts an outer surface of the instrument to be washed and preventing washing and rinsing fluid from contacting, hence cleaning and rinsing, the portion of the instrument that is received in the fitting on the clamp.

The present invention provides a new and improved construction which overcomes the above-referenced problems and others.

SUMMARY OF THE INVENTION

In accordance with one aspect of the present invention, there is provided a washer including a washing chamber having jets for spraying a washing and rinsing liquid into the washing chamber, and an instrument basket positioned within the washing chamber for retaining instruments or equipment to be washed. The washer further includes an instrument holder associated with the instrument basket for loosely holding an instrument. The instrument holder includes a tube body having a cavity for receiving an end portion of the instrument and a flange positioned on an external surface of the tube body. The instrument holder also includes a retainer cap removably retained on the tube body and having a resilient end wall covering an open end portion of the cavity. The end wall has a central aperture therein which resiliently yields to the instrument end portion when inserted in the cavity and which retains the instrument end portion sufficiently loosely that washing and rinsing liquids flow freely between the instrument end portion and retainer cap end wall during a washing and rinsing operation.

In accordance with a second aspect of the present invention, there is provided an instrument basket including a frame, a tube body for discharging washing and rinsing fluid, and a fluid manifold associated with the frame for supplying the washing and rinsing fluid to the tube body. The tube body includes a cavity for receiving at least a portion of an instrument therein and a flange positioned on an exterior surface of the tube body. The tube body also includes a retainer cap having an outer wall biased resiliently outwardly over the flange, and an end wall having a central aperture therein which resiliently yields to the instrument inserted in the cavity and which loosely retains the instrument during a washing and rinsing operation.

In accordance with a third aspect of the present invention, there is provided an instrument holder for use with an instrument basket positioned within a washing chamber of a washing device. The washing device includes a plurality of spray arms rotatably supported therein for spraying instruments retained in the instrument basket with washing and rinsing liquid. The instrument holder includes a tube body having a cavity defined therein, and a flange positioned on an external surface of the tube body. The instrument holder also includes a retainer cap having an outer wall frictionally engaged with the flange, and an end wall covering an open end portion of the cavity, the end wall having an aperture therein which resiliently yields to an instrument inserted in the cavity and which loosely retains the instrument in the cavity during a washing and rinsing operation.

In accordance with a fourth aspect of the present invention, there is provided a method of washing an instrument in a washing device having an instrument basket positioned within a washing chamber. The method includes the steps of positioning a retainer cap over a flange defined on an external surface of a tube body, the retainer cap having an end wall covering an open end portion of a cavity defined in the tube body, and having an aperture through the end wall, resiliently deforming the aperture with an instrument so as to position at least a portion of the instrument in the cavity, and discharging a cleaning and rinsing liquid into the cavity so as to direct a first portion of the liquid through a bore in the instrument and direct a second portion of the liquid through the aperture.

One advantage of the present invention is that all surfaces of the instruments or equipment to be washed are contacted with a washing and rinsing fluid.

Another advantage of the present invention is that it holds instruments and equipment in position adjacent a nozzle without engaging any surface in a washing or rinsing liquid blocking relationship.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

FIG. 3A is a diagrammatic view of a first embodiment of a cannula washer for use with the instrument basket shown in FIG. 2;

FIG. 3B is an end view of the cannula washer taken along the line 3B—3B in FIG. 3A;

FIG. 4A is a diagrammatic view of a second embodiment of a cannula washer for use with the instrument basket shown in FIG. 2;

FIG. 4B is an end view of the cannula washer taken along the line 4B—4B in FIG. 4A;

FIG. 4C is an enlarged correctional view showing transverse fluid passages of the cannula washer shown in FIG. 4A;

FIG. 5A is a diagrammatic view of a third embodiment of a cannula washer for use with the instrument basket shown in FIG. 2;

FIG. 5B is a threaded coupling associated with the cannula washer shown in FIG. 5A;

FIG. 5C is an end view of the cannula washer taken along the line 5C—5C in FIG. 5A;

FIG. 6A is a diagrammatic view of a retainer cap shown in FIG. 2;

FIG. 6B is an end view of the retainer cap taken along the line 6B—6B in FIG. 6A;

FIG. 7 is an expanded view of a suction instrument which is loosely retained by the retainer cap shown in FIGS. 6A and B in one of the cannula washers shown in FIGS. 3–5;

FIG. 10A is a diagrammatic view of a second embodiment of a retainer cap shown in FIG. 8;

FIG. 10B is an end view of the retainer cap taken along the line 10B—10B in FIG. 10A;

FIG. 11A is an elevational view of an instrument support member for use with the secondary instrument basket shown in FIG. 8;

FIG. 11B is a top view of the instrument support member taken along the line 11B—11B in FIG. 11A;

DETAILED DESCRIPTION OF THE PREFERRED EMBODIMENTS

Figure 1:
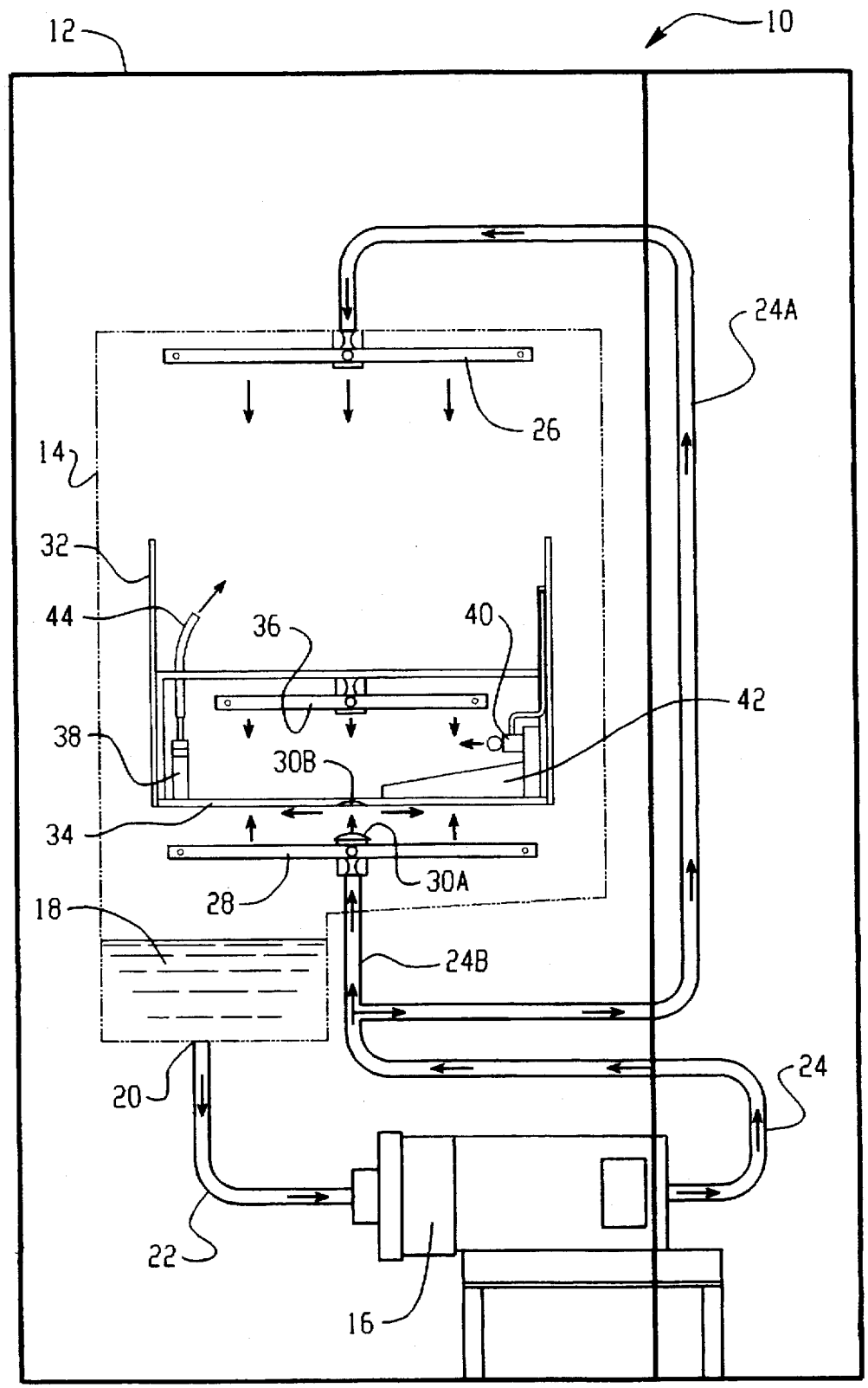
FIG. 1 is a diagrammatic illustration of a washing device which incorporates the features of the present invention therein.

With reference to FIG. 1, a washing device 10 includes a frame 12 for supporting a washing chamber 14 and a fluid pump 16. The washing chamber 14 includes a sump portion 18 having a drain 20 associated therewith. A first conduit 22 couples the drain 20 to an inlet portion of the fluid pump 16. A second conduit 24 couples an outlet of the fluid pump 16 to the washing chamber 14. In particular, the second conduit 24 includes a first portion 24A which couples washing and rinsing fluid to a first spray arm 26 rotatably positioned within the washing chamber 14, and a second portion 24B which couples washing and rinsing fluid to a second spray arm 28 rotatably positioned within the washing chamber 14. The first and second spray arms 26, 28 each include a plurality of nozzles or jets which may be defined as apertures in the spray arms, or by discrete nozzles or jets tapped into apertures in the spray arms 26, 28.

The second spray arm 28 includes a fluid coupling 30A which lifts under fluid pressure to couple with a mating portion 30B on a main instrument basket or rack assembly 32 which is positioned within the washing chamber 14. In particular, the fluid coupling 30A, 30B feeds washing and rinsing fluid under pressure to a conduit 34 which extends centrally along the width of the main instrument basket 32. As described in greater detail below, the conduit 34 couples washing and rinsing fluid to a third spray arm 36 rotatably secured to the main instrument basket 32, and couples washing and rinsing fluid to a plurality of first instrument holders 38 and to a plurality of second instrument holders 40 associated with a secondary instrument basket or rack assembly 42 which may be removably secured to the main instrument basket 32.

A suction-type instrument 44 is loosely retained to the instrument holder 38. The arrows indicate the discharge path of the washing and rinsing fluid, preferably water with detergents, wetting agents, or other additives, from the outlet of the fluid pump 16 to the first spray arm 26 through the conduit 24A, to the second spray arm 28 through the conduit 24B, and to the main instrument basket 32 through the fluid coupling 30A, 30B. The washing and rinsing fluid that is coupled to the conduit 34 of the main instrument basket 32 is discharged from the third spray arm 36, first instrument holders 38 and second instrument holders 40 in a manner described further below.

Figure 2:
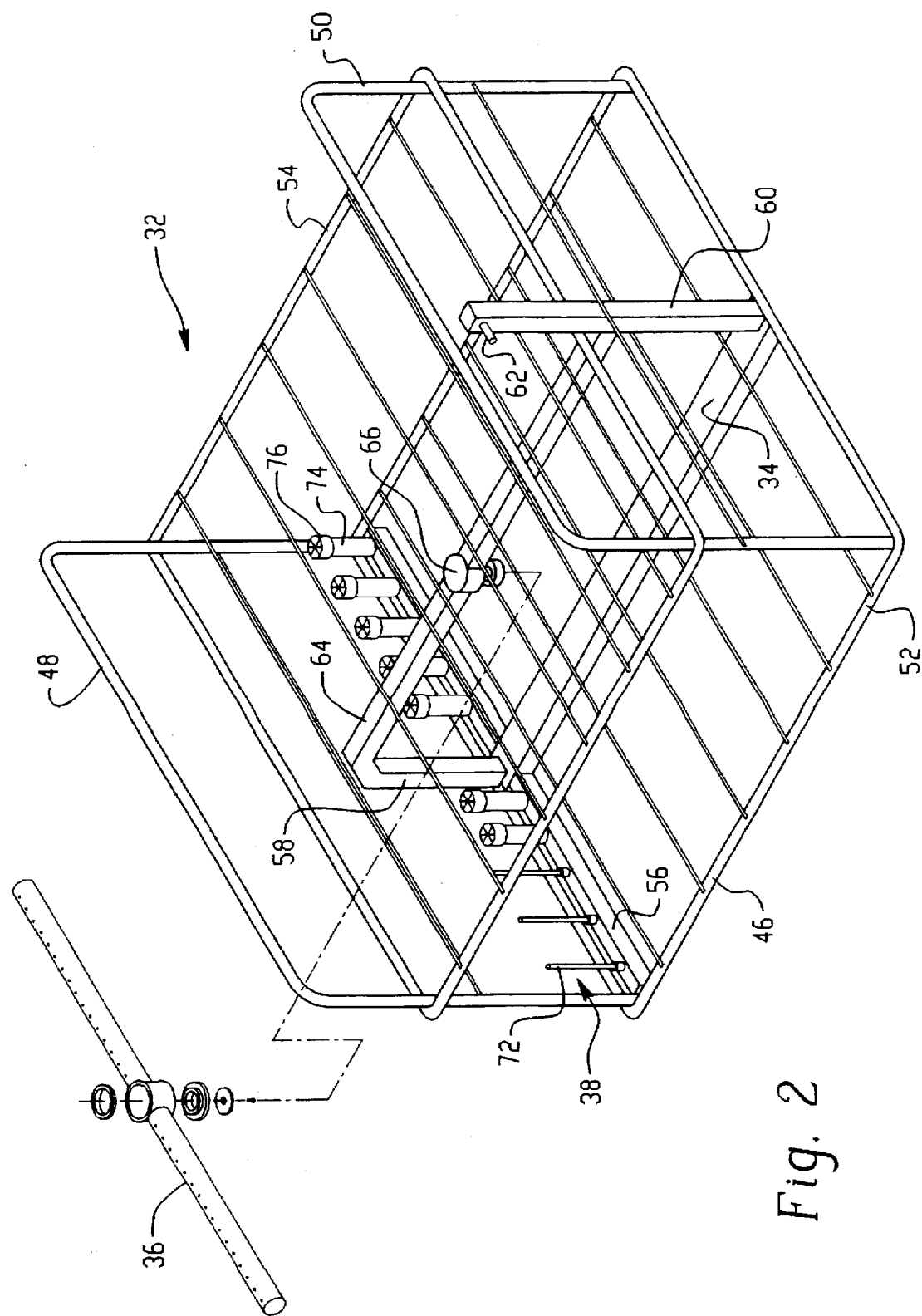
FIG. 2 is an expanded view illustrating an instrument basket or rack assembly shown in FIG. 1.

With continuing reference to FIG. 1 and particular reference to FIG. 2, a perspective view of the main instrument basket 32 is shown with the secondary instrument basket 42 removed therefrom. The main instrument basket 32 includes a substantially rectangular wire frame 46 having a first upright side portion 48 and a second upright side portion 50 joined to opposing ends of a first shelf 52 and a second shelf 54. The second shelf 54 is spaced apart from and above the first shelf 52.

A first fluid manifold 56 is joined to the first shelf 52 and extends along, and proximate to the first upright side portion 48. The conduit 34 communicates with a central portion of the first fluid manifold 56 and extends along the first shelf 52 in a direction transverse to the first fluid manifold 56. A first upright conduit 58 and a second upright conduit 60 communicate with opposing ends of the conduit 34. In particular, the first upright conduit 58 is secured to the first upright side portion 48 and communicates with the first fluid manifold 56. The second upright conduit 60 is secured to the second upright side portion 50 and communicates with the conduit 34 at an end thereof remote from the first fluid manifold 56. The second upright conduit 60 includes a fluid coupling 62 which couples washing and rinsing fluid to the secondary instrument basket 42 when mounted to the main instrument basket 32 as discussed in detail below.

A third conduit 64 is secured to, and extends along the width of the second shelf 54 in a direction substantially parallel to the conduit 34. A first end of the third conduit 64 communicates with the first upright conduit 58, and a second end of the third conduit 64 communicates with the second upright conduit 60. The third conduit 64 also includes a fluid coupling 66 centrally positioned therein which couples washing and rinsing fluid to the third spray arm 36 which is rotatably supported on the fluid coupling 66.

The fluid manifold 56 includes a plurality of apertures which communicate with the instrument holders 38. A number of different types of instrument holders 38 may be secured to the fluid manifold 56, such as bottle washers 72 and cannula washers 74. Instruments and equipment such as test tubes, beakers, and the like, may be placed over the bottle washers 72 such that washing and rinsing fluid may be sprayed into contact with the inner surfaces of the instruments or equipment covering the bottle washers 72. The bottle washers 72 also serve to retain the instruments and equipment placed thereover. As described in greater detail below, the cannula washers 74 include an inner cavity for receiving a base portion of hollow or tubular instruments and equipment such as suction tubes and cannulas. The cannula washers 74 include retainer caps 76 which are secured to and cover open-ended portions of the inner cavities so as to loosely retain the base portions of the instruments and equipment in the inner cavities.

Referring now to FIGS. 3A and 3B, the cannula washer 74 includes a tube body 75 and an externally threaded end portion 78 which may be threadably received, bayonette coupled, press fit, or the like within an aperture of the fluid manifold 56. The cannula washer 74 also includes an internal cavity 80 which communicates with a first end of the tube body 75 and extends longitudinally toward the threaded end portion 78. The internal cavity 80 includes a frustoconically-shaped end portion 82 which tapers radially inwardly toward the threaded end portion 78. A central fluid passage 84 extends axially from the frustoconical end portion 82 through the threaded end portion 78 to communicate with a second end of the tube body 75. The tube body 75 further includes a flange or rim 86 secured to an external surface of the tube body 75. The flange 86 extends circumferentially continuously around an exterior surface of the tube body 75 at a position adjacent the first end of the tube body 75, which first end thereof is remote from the threaded end portion 78. The flange 86 tapers radially inwardly in a direction toward the first end of the tube body 75.

Referring now to FIGS. 4A–4C, in which like reference numerals refer to like structural components with the embodiment of FIGS. 3A and 3B with the addition of a prime designation, a cannula washer 74' includes a tube body 75, an externally threaded end portion 78'; and an internal cavity 80' extending longitudinally from a first end of the tube body 75'. The internal cavity 80' includes an annular end portion 88 having an annular outer wall 90, annular inner wall 92, and transverse end wall 94. The annular outer wall 90 tapers radially inwardly to the annular inner wall 92 in a direction toward the threaded end portion 78'. The annular inner wall 92 tapers radially outwardly from the transverse end wall 94 to the annular outer wall 90 in a direction toward the threaded end portion 78'.

The tube body 75' further includes a central fluid passage 96 which extends axially from the transverse end wall 94 through the threaded end portion 78' to communicate with a second end of the tube body 75'. The central fluid passage 96 also communicates with the internal cavity 80' through an aperture in the transverse end wall 94. The central fluid passage 96 includes a number of transverse fluid passages 98 which extend from an intermediate portion of the central fluid passage 96 to the annular inner wall 92 so as to communicate with the internal cavity 80'. In the embodiment being described, four (4) transverse fluid passages are circumferentially spaced apart on the annular inner wall 92 as shown in FIG. 4B.

Referring now to FIGS. 5A–5C, in which like reference numerals with FIGS. 3 and 4 refer to like structural components with the addition of a double-prime designation, the cannula washer 74" includes a tube body 75" and a nozzle coupling 102. The nozzle coupling 102 includes a first coupling portion 104 which threadably or otherwise connects with an aperture in the fluid manifold 56, and a second coupling portion 106 which threadably or otherwise connects with an internally threaded end portion 108 of the tube body 75". The nozzle coupling 102 also includes a central fluid passage 110 which communicates with and extends axially from a conical end surface 112 through the first and second coupling portions 104, 106 to a second end of the nozzle coupling 102. The central fluid passage 110 includes a plurality of transverse fluid passages 98" or other fluid outlets which extend from the conical end surface 112 to the central fluid passage 110.

The tube body 75" includes an inner cavity 80" which extends axially from a first end of the tube body 75". An inner end surface 114 of the cavity 80" tapers radially inwardly to communicate with the internally threaded end portion 108 which is adapted to threadably receive the second coupling portion 106 of the nozzle coupling 102. When the tube body 75" is threadably coupled to the nozzle coupling 102, the transverse fluid passages 98" communicate with the internal cavity 80".

Referring now to FIGS. 6A and 6B, the retainer cap 76 includes a longitudinally extending tubular wall 116 of relatively thick cross section and a transversely extending end wall 118 of relatively thin cross section. The end wall 118 includes a central aperture 120 extending therethrough and a plurality of transverse slits 122 which intersect with the aperture 120. The retainer cap 76 is adapted so as to receive the open end portion of the tube body 75, 75' or 75" therein. More particularly, when the retainer cap 76 is positioned over an open-end portion of the tube body 75, 75' or 75", an open-end surface of the tube body 75, 75' or 75" abuts against the end wall 118 of the retainer cap 76, and the tubular walls 116 are urged resiliently, radially outwardly so as to conform to the circumferentially continuous flange 86, 86' or 86". The retainer cap 76 is held in place over the open-end portion of the tube body 75, 75' or 75" by a friction fit which is established between the flange 86, 86' or 86" and the tubular walls 116.

The transverse slits 122 cooperate to define a plurality of pie-shaped flap portions 124 which permit an end portion of an instrument or equipment to be positioned within the internal cavity 80, 80' or 80" as described further below. Optionally, structures may be placed at or between the ends of the slits to adjust the spring tension of the flaps. For instance, cut outs, slits, apertures, thin portions, hinge defining embossed lines reduce the spring tension. Thicker material, ribs, and the like increase the spring tension.

Referring now to FIG. 7, an exemplary suction tube 44 has a base portion 126 at a first end. With the retainer cap 76 positioned over the tube body 75, 75' or 75", the base portion 126 is urged through the end wall 118 so as to be positioned within the internal cavity 80, 80' or 80". More particularly, the base portion 126 is urged into the cavity 80, 80' or 80" so as to deform and/or deflect the flap portions 124 inwardly. Once the base portion 126 has past through the flap portions 124, the flap portions 124 are resiliently urged towards a closed position so as to frictionally retain the suction tube 44 within the cavity 80, 80' or 80".

When washing and rinsing fluids are pumped through the fluid manifold 56, washing and rinsing fluid is forced through the central fluid passage 84, 96, 110 of the cannula washer 74, 74' or 74", a portion of the washing and rinsing fluids are forced through the suction tube 44 while a remaining portion of the washing and rinsing fluids are forced around the outer surfaces of the base portion 126, thus contacting all of the surfaces of the suction tube 44. The flap portions 124 also serve to create a back pressure of washing and rinsing fluid in the cavity 80, 80' or 80" which permits washing and rinsing fluid to be forcibly ejected between the flap portions 124 of the retainer cap 76 and exterior surfaces of the suction tube 44. As one flap yields to the fluid pressure, the pressure distribution around the suction tube 44 changes causing it to wobble. The wobbling changes the contact force with other flaps allowing fluid to flow between other flaps and suction tube to assure all surfaces are washed.

Figure 8:
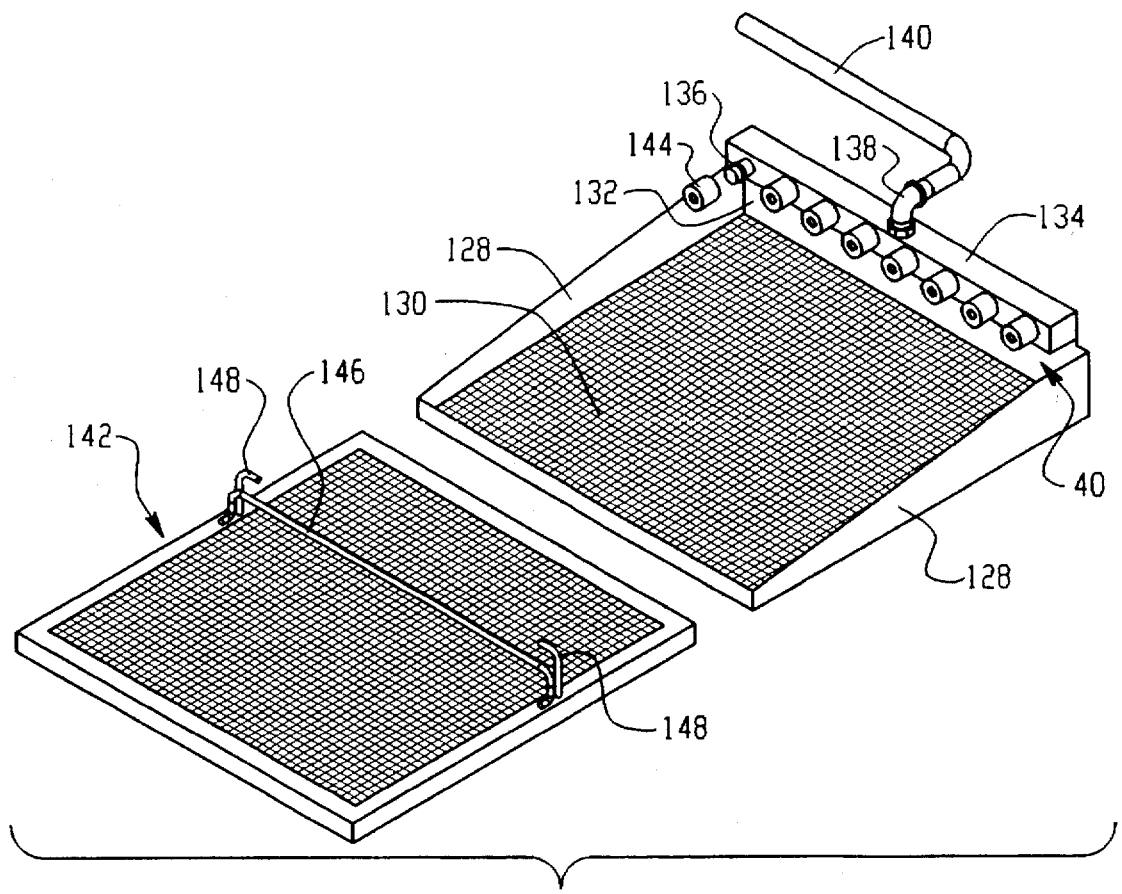
FIG. 8 is an expanded perspective view of a secondary instrument basket shown in FIG. 1.

Referring now to FIG. 8, the secondary instrument basket 42 is removed from within the main instrument basket 32. The secondary instrument basket 42 includes two tapered side walls 128 which are secured to opposing ends of a meshed lower surface 130. An end wall 132 extends between the side walls 128 and defines a fluid manifold 134. The fluid manifold 134 has a plurality of apertures extending therethrough which receive the second instrument holders 40 therein. A number of different types of instrument holders 40 may be secured to and communicate with the fluid manifold 134 such as cannula washers 136. The fluid manifold 134 also includes an inlet aperture for receiving an elbow coupling 138 therein. An elastomeric fluid supply hose 140 may connect a free end of the elbow coupling 138 with the fluid coupling 62 (FIG. 2) of the second upright conduit 60.

The secondary instrument basket 42 also includes a meshed cover 142 which may be positioned over the tapered side walls 128 so as to rest below the fluid manifold 134 and cannula washers 136. A retainer cap 144 frictionally engages with the cannula washers 136 in a manner similar to the retainer cap 76 discussed above. The mesh cover 142 includes a support bar 146 which extends along the width of the cover 142 for use in supporting an end portion of the tubular instruments or equipment that are loosely retained by the retainer caps 144. The support bar 146 includes L-shaped end portions 148 which serve to prevent the instruments and equipment from sliding off of the support bar 146. Non-tubular associated parts are placed on the mesh lower surface 130 and retained by the cover 142.

Figures 9A, 9B:
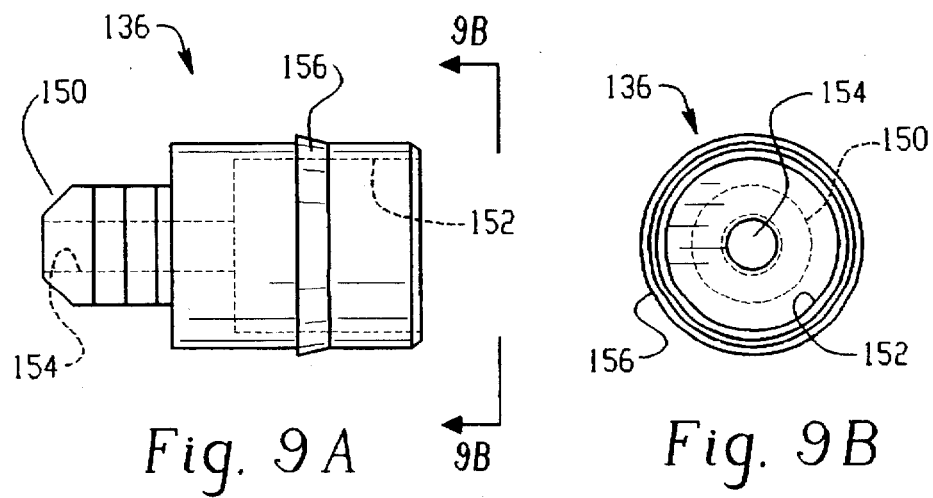
FIG. 9A is a diagrammatic view of a forth embodiment of a cannula washer for use with the secondary instrument basket shown in FIG. 8.
FIG. 9B is an end view of the cannula washer taken along the line 9B—9B in FIG. 9A.

Referring now to FIGS. 9A and 9B, there is shown a fourth embodiment of a cannula washers 136. As with the cannula washers 74, 74' or 74", the cannula washers 136 includes a tube body 149 having an end portion 150 which may be press fit or threadably engaged with the apertures extending through the fluid manifold 134. The tube body 149 also includes an inner cavity 152 which communicates with an open-end surface of the tube body 149. A central fluid passage 154 communicates with and extends from an inner surface of the cavity 152 through the end portion 150 to a second end of the tube body 149. The tube body 149 also includes a flange 156 secured to an external surface of the tube body 149. The flange 156 extends circumferentially continuously around the external surface at an intermediate position between the end portion 150 and the open-end surface of the tube body 149. It should be appreciated that the flanges 86, 86' or 86", 156 may be intermittently spaced around the exterior surface of the respective discharge jets 74, 74' or 74", 136.

Referring now to FIGS. 10A and 10B, a resilient retainer cap 144 includes a longitudinally extending tubular wall 158 of relatively thick cross section and a transverse end wall 160 of relatively thin cross section. The transverse end wall 160 includes an aperture 162 extending centrally therethrough. The aperture 162 is larger than a received instrument to provide washing flow around all surfaces of the instrument. As described below with reference to FIG. 12, the instrument has an enlarged end portion which is larger than the aperture 162 which is snapped through the resilient wall 160 for retention.

As described above with respect to the retainer cap 76, open an end surface of the tube body 149 abuts against the end wall 160 when the retainer cap 144 is positioned over the open-end surface of the tube body 149. The tubular walls 158 are urged resiliently outwardly so as to conform to the flange 156 on the exterior surface of the tube body 149. The retainer cap 144 is retained on the tube body 149 by a friction fit established between the tubular wall 158 and the flange 156 in abutting frictional engagement.

Referring now to FIGS. 11A and 11B, a secondary support arm 164 is preferably secured to the mesh cover 142 to provide additional or separating support for instruments and equipment which are loosely retained in the cavities 152 by the retainer caps 144. In particular, the secondary support arm 164 includes a number of spaced-apart V-shaped notches 166 which individually support a number of cannula-type instruments so that the cannula instruments do not contact each other during a washing and rinsing operation.

Figure 12A:
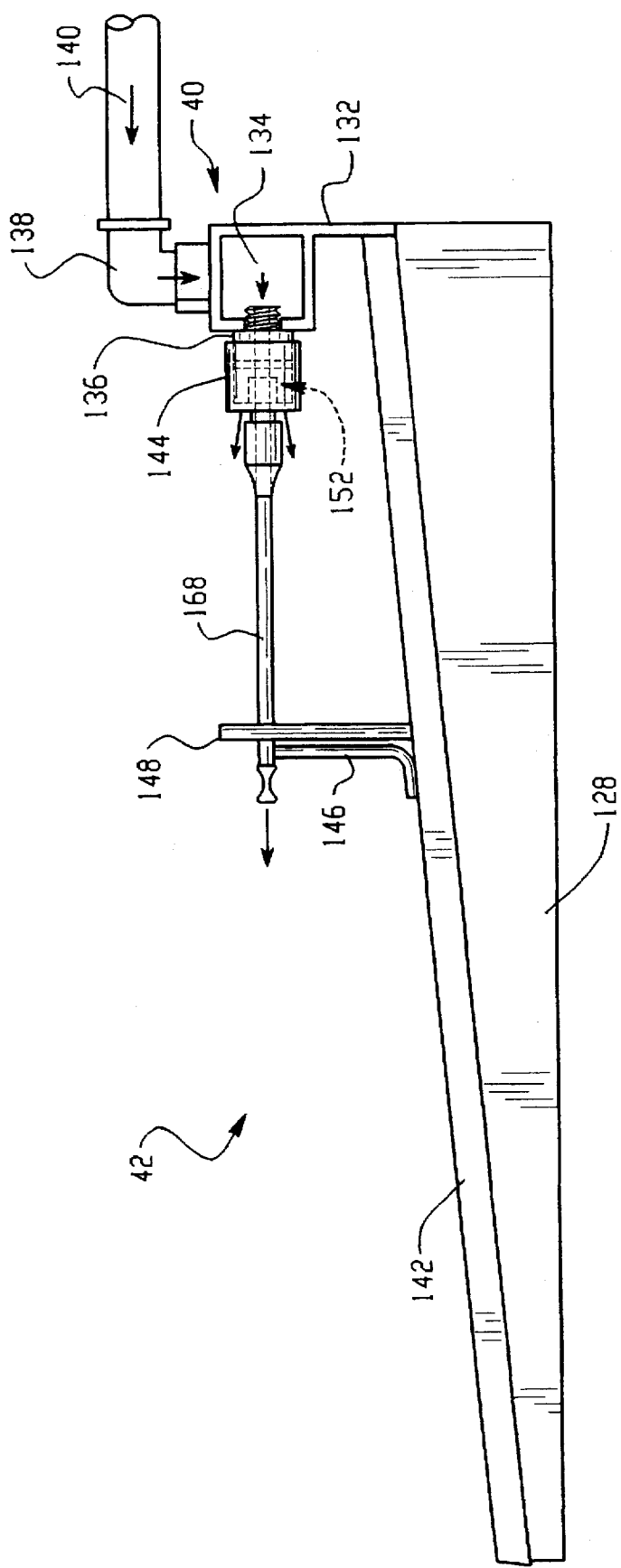
FIG. 12A is a diagrammatic view of the secondary instrument basket of FIG. 8 showing a cannula instrument loosely retained by the retainer cap shown in FIGS. 10A and 10B in the cannula washer shown in FIGS. 9A and 9B and supported by the instrument support member shown in FIGS. 11A and 11B.
Figure 12B:
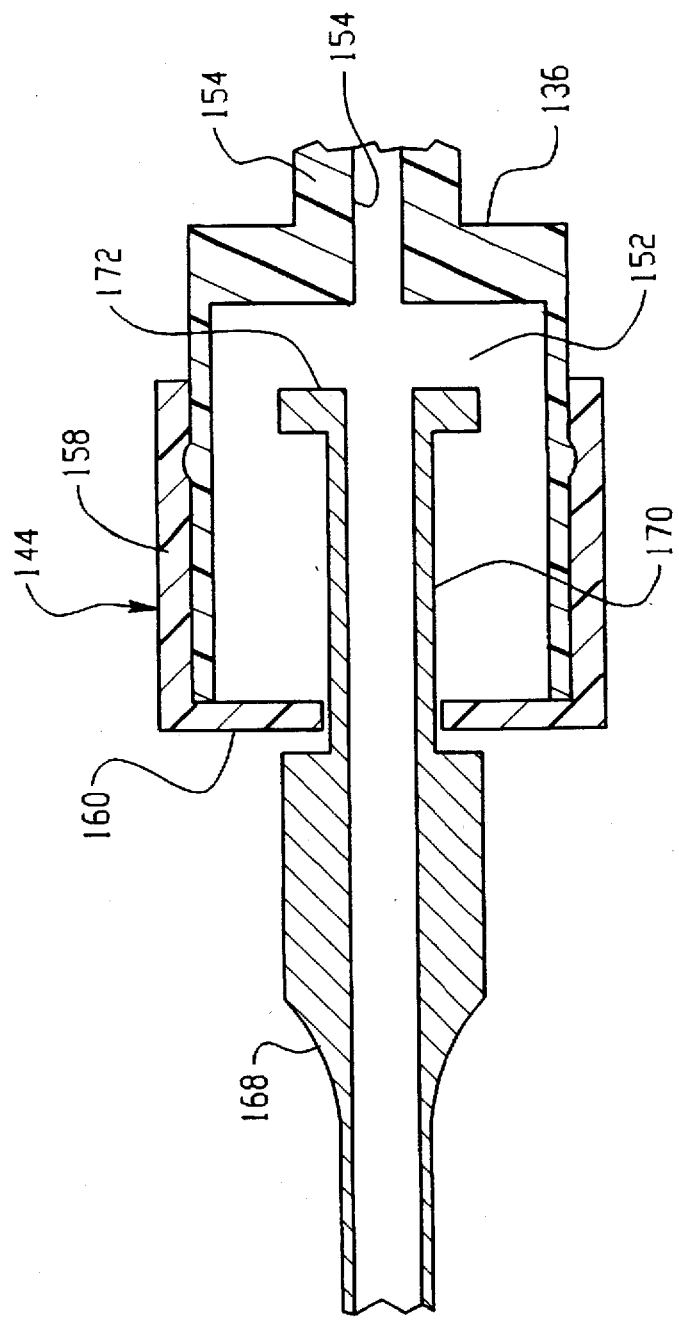
FIG. 12B is an enlarged diagrammatic view of the cannula instrument loosely in a cavity by the retainer cap.

Referring now to FIGS. 12A and 12B, the secondary instrument basket 42 is shown with the mesh cover 142 in place. An exemplary cannular instrument 168 having a narrower neck portion 170 and an enlarged base portion 172 is positioned within the internal cavity 152. In particular, the base portion 172 is urged through the aperture 162 in the retainer cap 144 that is frictionally retained on the tube body 149. It should be appreciated that the diameter of the aperture 162 is less than the diameter of the base portion 172. The end wall 160 resiliently yields to the base portion 172 by resiliently deflecting toward the cavity 152 until the base portion 172 passes through the aperture 162. Once the base portion 172 passes through the aperture 162, the end wall 160 is urged back to a resting position surrounding but spaced from the neck portion 170 so as to retain the instrument 168 loosely within the cavity 152.

When washing and rinsing fluid is pumped into the elastomeric fluid supply hose 140 and the fluid manifold 134, the washing and rinsing fluid is forcibly discharged from the central fluid passage 154 of the tube body 149. At least a portion of the washing and rinsing fluid is directed through an internal bore of the cannula instrument 168 to contact the inner surfaces thereof, while the remaining portion of the discharged washing and rinsing fluid will be directed along the exterior surfaces of the base portion 172 and be forcibly discharged through the aperture 162. The aperture 162 and end wall 160 serve to create a back pressure of washing and rinsing fluid within the cavity 152 so that the washing and rinsing fluid is forcibly ejected along the cannula instrument neck portion 170 thereby contacting the external surfaces thereof.

As shown in FIG. 12A, a proximal end of the cannula instrument 168 is supported and laterally restrained by the support bar 146 and L-shaped end portions 148.

It should be appreciated that the retainer caps 76, 144 loosely retain the respective instruments and equipment within the cavities 80, 80', 80", 152 of the tube bodies 74, 74', 74", 136 so that each and every surface of the instruments and equipment can be contacted by washing and rinsing fluid thereby thoroughly and efficiently washing the instruments and equipment.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed:

1. A washer including a washing chamber having jets for spraying a washing and rinsing liquid into the washing chamber, an instrument basket positioned within the washing chamber for retaining instruments or equipment to be washed, the washer further comprising:
   an instrument holder associated with the instrument basket for loosely holding an instrument, the instrument holder including:
      a tube body having a cavity for receiving an end portion of the instrument; and
      a retainer cap removably retained on the tube body, the retainer cap having a resilient end wall covering an open end portion of the tube body cavity, the end wall having a central aperture therein which resiliently yields to the instrument end portion when inserted in the cavity and which retains the instrument end portion sufficiently loosely that washing and rinsing liquids flow freely between the instrument end portion and the retainer cap end wall during a washing and rinsing operation.

2. The washer as set forth in claim 1, wherein the washer further includes:
   a fluid manifold for providing the washing and rinsing fluid to the tube body, the tube body including a fluid passage which communicates with the cavity at a first end thereof, and communicates with the fluid manifold at a second end thereof.

3. The washer as set forth in claim 2, wherein the cavity includes a frustoconical end portion which tapers toward and communicates with the fluid passage.

4. The washer as set forth in claim 2, wherein the cavity includes an annular end portion which tapers toward and communicates with the fluid passage.

5. The washer as set forth in claim 4, further including a plurality of transverse fluid passages which communicate with the annular end portion at one end thereof, and communicate with the fluid passage at a second end thereof.

6. The washer as set forth in claim 2, wherein the instrument holder further includes a coupler having a first end secured to the fluid manifold and a second end which communicates with the cavity.

7. The washer as set forth in claim 2, wherein the end wall includes slits therein which defines a plurality of flap portions which resiliently yield to the end portion when inserted in the cavity and which loosely retain the end portion in the cavity during a washing and rinsing operation.

8. The washer as set forth in claim 2, wherein the fluid manifold is secured to the instrument basket.

9. The washer as set forth in claim 8, further including a second instrument basket removably positioned within the first-mentioned instrument basket, the second instrument basket including:
   a second fluid manifold for supplying washing and rinsing fluid to a second instrument holder including a second tube body having a second cavity for receiving an end portion of an instrument, the second tube body being connected with the second manifold; and
   a second retainer cap having a second outer wall retained on the second tube body, and a second resilient end wall covering an open end portion of the second cavity, the second end wall having a second central aperture therein which resiliently yields to a second end portion of a second instrument inserted in the second cavity and which loosely retains the second end portion during a washing and rinsing operation.

10. The washer as set forth in claim 9, wherein the resilient end wall includes at least one slit therein which defines a plurality of flap portions for resiliently yielding to the first-mentioned end portion when inserted in the cavity and for loosely retaining the end portion in the cavity during a washing and rinsing operation.

11. The washer as set forth in claim 2, further including a second instrument basket removably positioned within the instrument basket, the fluid manifold being secured to the second instrument basket.

12. The washer as set forth in claim 11, further including a second fluid manifold for supplying washing and rinsing fluid to a second instrument holder including a second tube body having a second cavity for receiving a second end portion of a second instrument, and a second flange positioned on an external surface of the second tube body, the second instrument holder also including a second retainer cap having a second outer wall biased resiliently outwardly over the second flange, and a second end wall covering an open end portion of the second cavity, the second end wall having a second central aperture therein which resiliently yields to an instrument inserted in the second cavity and which loosely retains the instrument during the washing and rinsing operation.

13. The washer as set forth in claim 12 wherein the second end wall includes at least one slit therein which defines a plurality of flap portions which resiliently yield to the second end portion when inserted in the second cavity and which loosely retain the second end portion in the second cavity during a washing and rinsing operation.

14. An instrument basket comprising:
   a frame;
   a tube body for discharging washing and rinsing fluid;
   a fluid manifold associated with the frame for supplying the washing and rinsing fluid to the tube body;
   the tube body including a cavity for receiving at least a portion of an instrument therein and a flange positioned on an exterior surface of the tube body; and
   a retainer cap having an outer wall biased resiliently outwardly over the flange, and an end wall having a central aperture therein which resiliently yields to the instrument inserted in the cavity and which loosely retains the instrument during a washing and rinsing operation.

15. The instrument basket set forth in claim 14, wherein the fluid manifold is secured to the instrument basket, and wherein the end wall includes at least one slit therein which defines a plurality of flap portions which resiliently yield to the instrument when inserted in the cavity and which loosely retain the instrument in the cavity during a washing and rinsing operation.

16. The instrument basket set forth in claim 15, further including a secondary instrument basket removably secured to the frame and including a second tube body for discharging washing and rinsing fluid, a second fluid manifold associated with the secondary instrument basket for supplying washing and rinsing fluid to the second tube body, the second tube body having a second cavity for receiving at least a portion of a second instrument therein and a second flange positioned on an exterior surface of the second tube body, and a second retainer cap having a second outer wall biased resiliently outwardly over the second flange and a second end wall having a second aperture therein which resiliently yields to the second instrument inserted in the second cavity and which loosely retains the second instrument during a washing and rinsing operation.

17. The instrument basket set forth in claim 15, further including a secondary instrument basket removably secured to the frame, the fluid manifold being secured to the secondary instrument basket.

18. The instrument basket set forth in claim 17 further including a second tube body for discharging washing and rinsing fluid, a second fluid manifold secured to the frame for supplying washing and rinsing fluid to the second tube body, the second tube body having a second cavity for receiving at least a portion of a second instrument therein and a second flange positioned on an exterior surface of the second tube body, and a second retainer cap having a second outer wall biased resiliently outwardly over the second flange and a second end wall having a second aperture therein and at least one slit which defines a plurality of flap portions which resiliently yield to the second instrument when inserted in the second cavity and which loosely retain the second instrument in the second cavity during a washing and rinsing operation.

19. An instrument holder for use with an instrument basket positioned within a washing chamber of a washing device, the washing device including a plurality of nozzles for spraying instruments retained in the instrument basket with washing and rinsing liquid, the instrument holder comprising:

a tube body having a cavity defined therein, and a flange positioned on an external surface of the tube body; and a retainer cap having an outer wall frictionally engaged with the flange, and an end wall covering an open end portion of the cavity, the end wall having an aperture therein which resiliently yields to an instrument inserted in the cavity and which loosely retains the instrument in the cavity during a washing and rinsing operation.

20. The instrument holder set forth in claim 19, wherein the end wall includes at least one slit therein which defines a plurality of resilient flap portions.

21. A method of washing an instrument in a washing device having an instrument basket positioned within a washing chamber, comprising the steps of:

positioning a retainer cap over an open end of a tube body, the retainer cap having an end wall covering the open end of a cavity defined in the tube body, and having an aperture through the end wall;

resiliently deforming the end wall with an instrument so as to position at least a portion of the instrument in the cavity; and discharging a cleaning and rinsing liquid into the cavity so as to direct a first portion of the liquid through a bore in the instrument and direct a second portion of the liquid between the end wall and the instrument.

* * * * *